(12) United States Patent
Greenwald

(10) Patent No.: US 9,308,261 B2
(45) Date of Patent: Apr. 12, 2016

(54) COMPOSITIONS AND METHODS FOR TREATING VARICOSE VEINS

(75) Inventor: Sarah Steinberg Greenwald, Jerusalem (IL)

(73) Assignee: PREGNANT PRINCESS & CO. LTD., Jerusalem (IL)

( * ) Notice: Subject to any disclaimer, the term of this patent is extended or adjusted under 35 U.S.C. 154(b) by 444 days.

(21) Appl. No.: 13/123,529

(22) PCT Filed: Oct. 12, 2009

(86) PCT No.: PCT/IL2009/000974
§ 371 (c)(1),
(2), (4) Date: Apr. 10, 2011

(87) PCT Pub. No.: WO2010/044085
PCT Pub. Date: Apr. 22, 2010

(65) Prior Publication Data
US 2011/0196031 A1     Aug. 11, 2011

Related U.S. Application Data

(60) Provisional application No. 61/104,775, filed on Oct. 13, 2008.

(51) Int. Cl.
| | | |
|---|---|---|
| *A61K 31/355* | (2006.01) | |
| *A61P 43/00* | (2006.01) | |
| *A61K 45/06* | (2006.01) | |
| *A61K 9/68* | (2006.01) | |
| *A61K 9/20* | (2006.01) | |
| *A61K 9/51* | (2006.01) | |
| *A61K 31/202* | (2006.01) | |
| *A61K 31/215* | (2006.01) | |
| *A61K 31/375* | (2006.01) | |

(52) U.S. Cl.
CPC ............. *A61K 45/06* (2013.01); *A61K 9/0058* (2013.01); *A61K 9/2018* (2013.01); *A61K 9/5123* (2013.01); *A61K 31/202* (2013.01); *A61K 31/215* (2013.01); *A61K 31/355* (2013.01); *A61K 31/375* (2013.01)

(58) Field of Classification Search
None
See application file for complete search history.

(56) References Cited

U.S. PATENT DOCUMENTS

| | | | | |
|---|---|---|---|---|
| 5,968,896 A | * | 10/1999 | Bell et al. | 514/5.5 |
| 5,972,999 A | | 10/1999 | Murad | |
| 6,048,846 A | * | 4/2000 | Cochran | 514/168 |
| 6,140,304 A | | 10/2000 | Sears | |
| 6,800,292 B1 | * | 10/2004 | Murad | 424/401 |
| 7,226,916 B1 | * | 6/2007 | Kiliaan et al. | 514/165 |
| 2005/0261367 A1 | * | 11/2005 | Murad | 514/492 |
| 2007/0098787 A1 | * | 5/2007 | Kakiuchi | 424/464 |

OTHER PUBLICATIONS

'Vitamin Converter' in http://www.robert-forbes.com/resources/vitamin converter.html (accessed from the internet on Nov. 28, 2012).*
'Livestrong.com' in www.livestrong.com/ article/430013-does-canola-oil-have-omega-6-fatty-acids/ (accessed from the internet on Nov. 28, 2012).*
Linoleic Acid in www.linoleicacid.net (accessed from the internet on Nov. 28, 2012).*
Mayo Clinic in www.mayoclinic.com/health/varicose-veins/DS00256/DSECTION=prevention (accessed from the internet on Nov. 29, 2012).*
The Murad Method, St. Martin's Press (2003).*
Varicose veins and spider veins fact sheet in www.womenshealth.gov/ publications/our-publications/fact-sheet/varicose-spider-veins.cfm (retrieved from the internet Jun. 18, 2013).*
gamma-Linolenic Acid in en.wikipedia.org/wiki/ Gamma-Linolenic_acid (retrieved from the internet Jun. 18, 2013).*
Menon et al. in Advance in Experimental Medicine and Biology 595, 105-125 (2007).*
"ameliorate definition" in www.thefreedictionary.com/ameliorate (accessed from the internet on Jan. 5, 2014).*

* cited by examiner

*Primary Examiner* — Dennis Heyer
(74) *Attorney, Agent, or Firm* — Mark Cohen; Pearl Cohen; Zedek Latzer Baratz

(57) ABSTRACT

The present invention provides compositions and methods for preventing or treating diseases and disorders, the composition comprising vitamin C, vitamin E, and at least one of an omega-3 fatty acid and an omega-6 fatty acid.

40 Claims, No Drawings

COMPOSITIONS AND METHODS FOR TREATING VARICOSE VEINS

CROSS-REFERENCE TO RELATED APPLICATIONS

The current application is a U.S. National Phase Application under 35 U.S.C. 371 of PCT International Application No. PCT/IL2009/000974, which has an international filing date of Oct. 12, 2009, and which claims the benefit of priority from U.S. Provisional Patent Application No. 61/104,775, filed Oct. 13, 2008, the disclosures of which are incorporated herein by reference.

FIELD OF THE INVENTION

The present invention relates generally to compositions and methods for improving blood circulation, and more specifically to compositions and methods for preventing or treating varicose veins.

BACKGROUND OF THE INVENTION

Many people suffer from poor blood circulation. Poor blood circulation can result from insufficient pumping by the heart, aging, cardiovascular disease and lack of physical activity. Poor blood circulation may also lead to accumulation of liquids in the legs and lungs, and to varicose veins. Varicose veins are veins that are enlarged and twisted, often seen in the legs. Varicose veins are caused by anything that obstructs or partially restricts blood flow to the heart so that the blood dams up in the area of veins before the obstruction and ultimately become enlarged and twisted.

Varicose veins may be caused by poor blood circulation. Arteries carry blood from the heart to the rest of the tissues in the body. Veins return the blood from the rest of the body to the heart, in order to re-circulate the blood. Thus, the veins in the legs must work against gravity. Muscle contractions in the lower legs act as pumps, while toned, elastic vein walls help blood return to the heart. Minute one-way valves in the veins open as blood flows toward the heart then close to stop blood from flowing backwards.

Varicose veins may occur when the vein valves malfunction. Risk factors for varicose veins include:
a) Age—aging causes wear and tear on the vein valves which help regulate blood flow. Eventually, aging and wear cause the valves to malfunction.
b) Sex—women are more likely than men are to develop the condition, particularly during pregnancy.
c) Genetics—there is a genetic predisposition to varicose veins such that it runs in families.
d) Obesity—being overweight adds pressure to the veins, particularly in the legs.
e) Standing for long periods of time—blood does not flow well in a stationary body.

As one ages, ones veins may lose elasticity, causing them to stretch. When this happens, the blood does not move towards the heart, but instead may flow backwards, thus forming blood pools in the veins. The veins thereby become enlarged and varicose. The varicose veins appear blue because they contain deoxygenated blood, which is in the process of being re-circulated.

The development of varicose veins may be prevented to some degree by avoiding factors which restrict blood flow through veins, such as by not wearing socks or stockings that are too tight.

The symptoms of varicose veins can be controlled to some extent by raising the legs and bed rest. The wearing of graduated compression stockings with a pressure of 30-40 mmHg has been shown to correct the swelling, nutritional exchange, and improve the microcirculation in legs affected by varicose veins.

The treatment of varicose veins is divided into surgical and non-surgical treatment. Non-surgical treatment may include anti-inflammatory medication, such as ibuprofen or aspirin, can be used as part of treatment for superficial thrombophlebitis along with graduated compression hosiery. Diosmin 95 is a semisynthetic phlebotropic drug, a member of the flavonoid family, and is used as a dietary supplement. It is distributed in the U.S. by Nutratech, Inc.

Options for surgical treatment include traditional open surgery and newer methods. Newer methods for treating varicose veins include endovenous laser treatment, radiofrequency ablation, and foam Complications of open surgery include deep vein thrombosis, pulmonary embolism, and wound complications including infection. There is thus a need to develop new compositions and formulations for treating varicose veins.

Other types of varicose veins include:
a. Venous lakes. These are pools of blood in the veins, often found on the face and neck.
b. Reticular veins. These flat, blue veins under the skin often appear behind the knee.
c. Telangiectases. These are fine clusters of blood vessels similar to spider veins, reddish in color and often found on the face or upper body.

Spider veins are similar to varicose veins, but they are smaller. They are often red or blue and are closer to the surface of the skin than varicose veins. They can look like tree branches or spider webs with their short jagged lines. Spider veins can be found on the legs and face. They can cover either a very small or very large area of skin.

There thus remains a need to develop new compositions and formulations for treating varicose veins. Various patent applications describe compositions and methods for treating blood circulatory problems and varicose veins are listed hereinbelow.

U.S. Pat. No. 4,612,194, to Roshdy et al., disclose anti-rheumatic agents containing vitamin E in combination with vasodilators and/or blood circulation-promoting agents. A method of treating rheumatic diseases is also disclosed.

BG106384U, to Kamburov et al., discloses a prophylactic means as an additive to the daily human diet. It is recommended for improving the functions of the lymphatic and venous system, in danger of varicose veins and haemorrhoids, as it is an antioxidant and reinforces the immune system. The means is made in the form of solid gelatine capsules, containing homogenous mixture of the following component content, in wt. %: dry extract of yellow meliot 11.25-13.75; mixture of vitamins and microelements: vitamin A 0.17-0.20; vitamin C 11.25-13.75; vitamin E 2.25-2.75; iron (sulphate) 0.056-0.068; manganese (sulphate) 0.056-0.068; zinc (sulphate) 0.11-0.13; mannitol 30.90-34.30; lactic sugar 16.40-20.07; talcum 14.40-20.07; magnesium stearate 1.12-1.37 and aerosil 1.68-2.06.

BG105585U, also to Kamburov et al., discloses a means made in the form of solid gelatine capsules, for use as an additive to the daily diet. It is recommended for increasing the organism resistance against atherosclerosis, in cardiovascular disorders, overweight and for maintaining good vision, including in diabetic retinopathy. It is used for the prophylactics of malignant cell alterations, varicose veins, as well as of inflammation such as arthritis and allergies. The solid gelatine capsules are homogenous mixture of dry extract of grape seeds and mixture of vitamins A, C and E, and the microelements of iron, manganese and zinc, with the following content of the components, in wt. %: dry extract of grape seeds from 28.12 to 34.37, mixture of vitamins and microelements: vitamin A 0.17-0.20, vitamin C from 11.25 to 13.75, vitamin E 2.25-2.75, iron (sulphate) 0.05-0.07, manganese (sulphate) 0.05-0.07, zinc (sulphate) 0.011-0.013, mannitol 28.12 to 34.37, lactic sugar 5.62-6.87, talcum from 11.24 to 13.74, magnesium stearate 1.68-2.06 and aerosil 1.12-1.37.

U.S. Pat. No. 7,226,916, issued to Kiliaan et al., discloses a preparation suitable for the prevention and/or treatment of vascular disorders, comprising the following fractions: fraction a) consisting of long chain polyunsaturated fatty acids; fraction b) consisting of phospholipids, which fraction contains at least two different phospholipids selected from the group consisting of phosphatidylserine, phosphatidylinositol, phosphatidylcholine and phosphatidylethanolamine. fraction c) consisting of compounds which are a factor in methionine metabolism, which fraction contains at least one member selected from the group consisting of folic acid, vitamin B12, vitamin B6, magnesium and zinc.

There are many food supplements and vitamins available commercially for improving blood circulation, in general, but there is a lack of compositions and methods for treating varicose veins.

SUMMARY OF THE INVENTION

It is an object of some aspects of the present invention to provide compositions for improving wellness in a human or mammalian organism.

It is another object of some aspects of the present invention to provide compositions for preventing or treating diseases or disorders in a human or mammalian organism.

It is another object of some aspects of the present invention to provide compositions for improving blood circulation.

It is another object of some aspects of the present invention to provide compositions for treating or preventing varicose veins.

It is an object of some aspects of the present invention to provide methods for improving blood circulation.

It is another object of some aspects of the present invention to provide compositions and methods for preventing the occurrence of varicose veins.

In some embodiments of the present invention, compositions are provided for preventing or treating varicose veins.

In other embodiments of the present invention, methods for treating varicose veins are provided.

According to some embodiments of the present invention, the composition comprises at least one fatty acid, vitamin C and vitamin E in a predetermined ratio. All the aforementioned components may be from a natural source, a semi-synthetic source, a synthetic source or combinations thereof. The compositions may be provided in by any suitable means to the patient or subject, such as, but not limited to, oral dosage form, injection, dermal patch and spray.

According to further embodiments, the composition comprises at least two fatty acids, vitamin C and vitamin E in a predetermined ratio.

According to some embodiments, the fatty acids are unsaturated. Preferably, the fatty acids comprise poly-unsaturated fatty acids, more preferably, long-chain polyunsaturated fatty acids (LC-PUFA).

The long chain polyunsaturated fatty acids may comprise one or more omega-3 fatty acids (ω-3 fatty acids), may, according to some embodiments, be selected from eicosapentaenoic acid (EPA (20:5)), Eicosatetraenoic acid (ETA), and docosahexaenoic acid (DHA (22:6)).

The long chain polyunsaturated fatty acids may comprise one or more omega-6 fatty acids (ω-6 fatty acids). According to some embodiments, the omega-6 fatty acids are selected from gamma-linolenic acid (GLA (18:3)), dihomo-gamma-linolenic acid (DGLA (20:3)) and arachidonic acid (AA (20:4)).

The compositions and dosage forms of the present invention are useful in promoting health and preventing or treating a large number of disorders in human patients and other mammalian subjects.

In additional embodiments of the present invention, compositions and methods are provided for treating and/or preventing heart disease, such as, but not limited to, atherosclerotic and hypertensive diseases, congenital heart disease, rheumatic heart disease, and other conditions.

In further embodiments of the present invention, compositions and methods are provided for treating and/or preventing peripheral blood vessel disorders. Peripheral blood vessel disorders affect the blood vessels of the arms, legs, and trunk (except those supplying the heart). These disorders include disorders of the blood vessels supplying the brain, namely cerebrovascular disorders.

In additional embodiments of the present invention, compositions and methods are provided for treating and/or preventing blood disorders, In additional embodiments of the present invention, compositions and methods are provided for treating and/or preventing disorders of nutrition or metabolism.

In additional embodiments of the present invention, compositions and methods are provided for treating and/or preventing hormonal disorders.

In additional embodiments of the present invention, compositions and methods are provided for treating and/or preventing bone, joint or muscle disorders.

In additional embodiments of the present invention, compositions and methods are provided for treating and/or preventing brain, spinal cord or nervous disorders.

In additional embodiments of the present invention, compositions and methods are provided for treating and/or preventing immunological disorders.

In additional embodiments of the present invention, compositions and methods are provided for treating and/or preventing infectious disorders.

In additional embodiments of the present invention, compositions and methods are provided for treating and/or preventing urinary tract and kidney disorders.

In additional embodiments of the present invention, compositions and methods are provided for treating and/or preventing skin disorders.

In additional embodiments of the present invention, compositions and methods are provided for treating and/or preventing vitamin deficiencies and other nutritional disorders.

In additional embodiments of the present invention, compositions and methods are provided for treating and/or preventing lung or airway disorders.

In additional embodiments of the present invention, compositions and methods are provided for treating and/or preventing digestive disorders.

In additional embodiments of the present invention, compositions and methods are provided for treating and/or preventing reproductive disorders.

There is thus provided according to some embodiments of the present invention, a composition for treating or preventing a disease or disorder, the composition including vitamin C, vitamin E, and at least one of an omega-3 fatty acid and an omega-6 fatty acid.

According to some embodiments, the composition includes at least one omega-3 fatty acid and at least one omega-6 fatty acid.

According to some further embodiments, the composition includes, per tablet:
10-3000 mg vitamin C;
10-1000 IU Vitamin E;
10-1000 mg Omega-3 fatty acid; and
1-100 mg Omega-6 fatty acid.

According to some further embodiments, the composition includes, per tablet:
10-3000 mg vitamin C;
10-1000 IU Vitamin E;
1-1000 mg Omega-3 fatty acid; and
1-100 mg Omega-6 fatty acid.

According to yet some further embodiments, the composition includes, per tablet:
20-1000 mg vitamin C;
20-500 IU Vitamin E;
20-500 mg Omega-3 fatty acid; and
5-50 mg Omega-6 fatty acid.

According to some additional embodiments, the composition includes, per tablet:
200-500 mg vitamin C;
200-500 IU Vitamin E;
20-200 mg Omega-3 fatty acid; and
5-20 mg Omega-6 fatty acid.

In certain embodiments, the composition includes one of the above amounts of the ingredients per daily dosage.

In some cases, the omega 3 fatty acid is selected from eicosapentaenoic acid (EPA (20:5)), Eicosatetraenoic acid (ETA), and docosahexaenoic acid (DHA (22:6)).

According to some embodiments, the omega 6 fatty acid is selected from gamma-linolenic acid (GLA (18:3)), dihomo-gamma-linolenic acid (DGLA (20:3)) and arachidonic acid (AA (20:4)).

The compositions may be provided to the subject in an oral dosage form. In some cases, the oral dosage form includes a capsule.

In other embodiments, the oral dosage form may be chewable. The oral dosage form may further comprise at least one of fructose, sorbitol, microcrystalline cellulose, magnesium stearate, or a combination thereof.

In some cases, the oral dosage form includes at least one additional antioxidant. The oral dosage form may also include additional agents and components.

DETAILED DESCRIPTION OF PREFERRED EMBODIMENTS

The present invention is directed to compositions and methods for treating blood circulatory disorders, in general, and more particularly, varicose veins. The compositions of the present invention may be used for improving wellness of a human or mammalian subject. Additionally, the compositions of the present invention may be used to treat any disorder or ailment in a human patient or mammalian subject. Furthermore, the compositions of the present invention may conveniently used in conjunction with a drug to treat any disorder or ailment in a human patient or mammalian subject.

According to some embodiments of the present invention, the composition comprises at least one fatty acid, vitamin C and vitamin E in a predetermined ratio.

In another embodiment, this invention provides oral dosage forms comprising a composition which comprises vitamin C, vitamin E, and at least one fatty acid.

In another embodiment, this invention provides oral dosage forms comprising a composition which comprises vitamin C, vitamin E, and unsaturated fatty acids.

Vitamin E is a fat-soluble vitamin that exists in eight different forms. Each form has its own biological activity, which is the measure of potency or functional use in the body. The eight forms of vitamin E include four tocopherols (alpha-, beta-, gamma-, and delta-) and four tocotrienols (alpha-, beta-, gamma-, and delta-). Alpha-tocopherol is the only form of vitamin E that is actively maintained in the human body; therefore, it is the form of vitamin E found in the largest quantities in blood and tissues.

Vitamin C or L-ascorbate is an essential nutrient for a large number of higher primate species, a small number of other mammalian species.

According to further embodiments, the composition comprises at least two fatty acids, vitamin C and vitamin E in a predetermined ratio.

According to some embodiments, the fatty acids are unsaturated. Preferably, the fatty acids comprise poly-unsaturated fatty acids, more preferably, long-chain polyunsaturated fatty acids (LC-PUFA).

The long chain polyunsaturated fatty acids may comprise one or more omega-3 fatty acids (ω-3 fatty acids) (see Table 1). According to some further embodiments, these ω-3 fatty acids may be selected from eicosapentaenoic acid (EPA (20:5)) and docosahexaenoic acid (DHA (22:6)).

TABLE 1

OMEGA-3 FATTY ACIDS

| Common name | Lipid name | Chemical name |
| --- | --- | --- |
|  | 16:3 (n-3) | all-cis-7,10,13-hexadecatrienoic acid |
| α-Linolenic acid (ALA) | 18:3 (n-3) | all-cis-9,12,15-octadecatrienoic acid |
| Stearidonic acid (STD) | 18:4 (n-3) | all-cis-6,9,12,15-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Docosapentaenoic acid (DPA), Clupanodonic acid | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |
| Tetracosapentaenoic acid | 24:5 (n-3) | all-cis-9,12,15,18,21-docosahexaenoic |

TABLE 1-continued

OMEGA-3 FATTY ACIDS

| Common name | Lipid name | Chemical name |
|---|---|---|
| Tetracosahexaenoic acid (Nisinic acid) | 24:6 (n-3) | all-cis-6,9,12,15,18,21-tetracosenoic acid |

The long chain polyunsaturated fatty acids may further comprise omega-6 (ω-6) fatty acids, such as any one or more listed herein in Table 2.

According to some embodiments, the omega-6 fatty acids are selected from gamma-linolenic acid (GLA (18:3)), dihomo-gamma-linolenic acid (DGLA (20:3)) and arachidonic acid (AA (20:4)).

TABLE 2

LIST OF OMEGA-6 (Ω-6) FATTY ACIDS

| Common name | Lipid name | Chemical name |
|---|---|---|
| Linoleic acid | 18:2 (n-6) | 9,12-octadecadienoic acid |
| Gamma-linolenic acid | 18:3 (n-6) | 6,9,12-octadecatrienoic acid |
| Eicosadienoic acid | 20:2 (n-6) | 11,14-eicosadienoic acid |
| Dihomo-gamma-linolenic acid | 20:3 (n-6) | 8,11,14-eicosatrienoic acid |
| Arachidonic acid | 20:4 (n-6) | 5,8,11,14-eicosatetraenoic acid |
| Docosadienoic acid | 22:2 (n-6) | 13,16-docosadienoic acid |
| Adrenic acid | 22:4 (n-6) | 7,10,13,16-docosatetraenoic acid |
| Docosapentaenoic acid | 22:5 (n-6) | 4,7,10,13,16-docosapentaenoic acid |
| Calendic acid | 18:3 (n-6) | 8E,10E,12Z-octadecatrienoic acid |

According to some embodiments, the vitamins and fatty acids described herein may be purchased commercially from suppliers such as, but not limited to, Sigma Chemicals, St. Louis, Mo., USA; AppliChem GmbH Darmstadt, Germany; Cayman Chemical, Ann Arbor, Mich. USA; or Dupont, Wilmington, Del., USA, etc.

According to some further embodiments, the vitamins and fatty acids described herein may be extracted from an animal and/or plant source.

According to some further embodiments, the vitamins and fatty acids described herein may be synthesized or produced by methods known in the art.

Vitamin C

Vitamin C may be produced according to any method known in the art today or by any future method. The vitamin C may be from a natural source, semi-synthetic source, synthetic source or combinations thereof. It may be extracted from one or more animal or vegetable sources, produced by fermentation, chemically synthesized or modified, or any combination of the aforesaid.

In another embodiment, vitamin C comprises the L-enantiomer of ascorbate.

According to some embodiments, vitamin C is provided as calcium ascorbate, which is non-acidic (pH neutral), making it gentle on the digestive system.

In some embodiments, vitamin C of the present invention is derived from meat. In another embodiment, vitamin C of the present invention is derived from liver. In some embodiments, vitamin C of the present invention is derived from fruits or vegetables. In another embodiment, vitamin C of the present invention is derived from camu camu fruit. In another embodiment, vitamin C of the present invention is derived from billygoat plum. In another embodiment, vitamin C of the present invention is derived from wolfberry. In another embodiment, vitamin C of the present invention is derived from rose hip. In another embodiment, vitamin C, of the present invention is derived from acerola. In another embodiment, vitamin C of the present invention is derived from amla. In another embodiment, vitamin C of the present invention is derived from jujube. In another embodiment, vitamin C of the present invention is derived from baobab. In another embodiment, vitamin C of the present invention is derived from blackcurrant. In another embodiment, vitamin C of the present invention is derived from red pepper. In another embodiment, vitamin C of the present invention is derived from parsley. In another embodiment, vitamin C of the present invention is derived from seabuckthorn. In another embodiment, vitamin C of the present invention is derived from guava. In another embodiment, vitamin C of the present invention is derived from kiwi. In another embodiment, vitamin C of the present invention is derived from broccoli. In another embodiment, vitamin C of the present invention is derived from longanberry. Each possibility represents a separate embodiment of the present invention.

In another embodiment, vitamin C is used as ascorbic acid is in the form of crystals. In another embodiment, vitamin C is in the form of various mineral ascorbates.

In another embodiment, vitamin C of the present invention is produced from glucose by one of two main routes. In another embodiment, the Reichstein process is used. In some embodiments, a two-step fermentation process is used. In another embodiment, the processes at least 40% vitamin C from the glucose feed. In another embodiment, the processes at least 50% vitamin C from the glucose feed. In another embodiment, the processes at least 60% vitamin C from the glucose feed. In another embodiment, the processes at least 70% vitamin C from the glucose feed. Each possibility represents a separate embodiment of the present invention.

According to some embodiments, the compositions of the present invention may comprise bioflavenoids instead of vitamin C.

According to yet some further embodiments, the compositions of the present invention may comprise natural sources of bioflavonoids, which also provide vitamin C.

In one embodiment, a dosage form of the present invention comprises 1-3000 mg vitamin C. In another embodiment, a dosage form of the present invention comprises 1-1000 mg vitamin C. In another, embodiment, a dosage form of the present invention comprises 2-300 mg vitamin C. In another, embodiment, a dosage form of the present invention comprises 2-50 mg vitamin C. In another, embodiment, a dosage form of the present invention comprises 30-80 mg vitamin C. In another, embodiment, a dosage form of the present invention comprises 50-100 mg vitamin C. In another, embodiment, a dosage form of the present invention comprises 75-150 mg vitamin C. In another, embodiment, a dosage form of the present invention comprises 150-250 mg vitamin C. In another, embodiment, a dosage form of the present invention comprises 200-300 mg vitamin C. In another, embodiment, a dosage form of the present invention comprises 250-300 mg vitamin C. In another, embodiment, a dosage form of the present invention comprises 250-400 mg vitamin C. In another, embodiment, a dosage form of the present invention comprises 250-350 mg vitamin C. In another, embodiment, a dosage form of the present invention comprises 300-500 mg vitamin C. In another, embodiment, a dosage form of the present invention comprises 350-500 mg vitamin C. In another, embodiment, a dosage form of the present invention comprises 400-500 mg vitamin C.

Vitamin E

Vitamin E in supplements may be purchased commercially as alpha-tocopheryl acetate, a form of alpha-tocopherol that protects its ability to function as an antioxidant, or in any other commercially available form.

The vitamin E may be from a natural source, semi-synthetic source, synthetic source or combinations thereof.

In one embodiment, a dosage form of the present invention comprises 1-1000 IU vitamin E. In another embodiment, a dosage form of the present invention comprises 1-500 IU vitamin E. In another, embodiment, a dosage form of the present invention comprises 2-300 IU vitamin E. In another, embodiment, a dosage form of the present invention comprises 2-50 IU vitamin E. In another, embodiment, a dosage form of the present invention comprises 30-80 IU vitamin E. In another, embodiment, a dosage form of the present invention comprises 50-100 IU vitamin E. In another, embodiment, a dosage form of the present invention comprises 75-150 IU vitamin E. In another, embodiment, a dosage form of the present invention comprises 150-250 IU vitamin E. In another, embodiment, a dosage form of the present invention comprises 200-300 IU vitamin E. In another, embodiment, a dosage form of the present invention comprises 250-300 IU vitamin E. In another, embodiment, a dosage form of the present invention comprises 250-400 IU vitamin E. In another, embodiment, a dosage form of the present invention comprises 250-350 IU vitamin E. In another, embodiment, a dosage form of the present invention comprises 300-500 IU vitamin E. In another, embodiment, a dosage form of the present invention comprises 350-500 IU vitamin E. In another, embodiment, a dosage form of the present invention comprises 400-500 IU) vitamin E.

EP0039830A1 describes a process for the preparation of optically active compounds and their use in the preparation of vitamin E, which is incorporated herein by reference.

Omega-3 Fatty Acids

Dietary sources of omega-3 fatty acids include fish oil and certain plant/nut oils. Fish oil contains both docosahexaenoic acid (DHA) and eicosapentaenoic acid (EPA), while some nuts (e.g., English walnuts) and vegetable oils (e.g., canola, soybean, flaxseed/linseed, and olive oil) contain alpha-linolenic acid (ALA).

U.S. Pat. No. 5,151,291A discloses glycerides of eicosapentaenoic acid (EPA) and other higher fatty acids, which contain high levels of EPA and docosahexaenoic acid. These glycerides are incorporated in oils and fats products such as margarine, shortening, mayonnaise, butter, dressing or edible oil.

In one embodiment, a dosage form of the present invention comprises 1-500 mg $\omega$-3 fatty acids. In another embodiment, a dosage form of the present invention comprises 1-300 mg $\omega$-3 fatty acids. In another, embodiment, a dosage form of the present invention comprises 2-200 mg $\omega$-3 fatty acids. In another, embodiment, a dosage form of the present invention comprises 2-100 mg $\omega$-3 fatty acids. In another, embodiment, a dosage form of the present invention comprises 20-80 mg $\omega$-3 fatty acids. In another, embodiment, a dosage form of the present invention comprises 50-100 mg $\omega$-3 fatty acids. In another, embodiment, a dosage form of the present invention comprises 30-80 mg $\omega$-3 fatty acids.

According to some embodiments, the $\omega$-3 fatty acids may be selected from any one or more of $\alpha$-Linolenic acid (ALA), Stearidonic acid (STD), Eicosatrienoic acid (ETE), Eicosatetraenoic acid (ETA), Eicosapentaenoic acid (EPA), Docosapentaenoic acid (DPA), Docosahexaenoic acid (DHA), Tetracosapentaenoic acid, and Tetracosahexaenoic acid (Nisinic acid).

Omega-6 Fatty Acids

According to some further embodiments, compositions and dosage forms of the present invention comprise one or more omega-6 ($\omega$-6) fatty acids the omega-6 fatty acids. The one or more omega-6 fatty acids may be selected from linoleic acid; gamma-linolenic acid; eicosadienoic acid; dihomo-gamma-linolenic acid; arachidonic acid; docosadienoic acid; adrenic acid; docosapentaenoic acid and calendic acid.

In one embodiment, a dosage form of the present invention comprises 1-100 mg $\omega$-6 fatty acids. In another embodiment, a dosage form of the present invention comprises 1-50 mg $\omega$-6 fatty acids. In another, embodiment, a dosage form of the present invention comprises 2-50 mg $\omega$-6 fatty acids. In another, embodiment, a dosage form of the present invention comprises 2-40 mg $\omega$-6 fatty acids. In another, embodiment, a dosage form of the present invention comprises 10-50 mg $\omega$-6 fatty acids. In another, embodiment, a dosage form of the present invention comprises 5-20 mg $\omega$-6 fatty acids. In another, embodiment, a dosage form of the present invention comprises 10-30 mg $\omega$-6 fatty acids.

Dosage Forms

The compositions of the present invention may be provided in any suitable dosage form. According to some embodiments, the dosage form is an oral dosage form. Oral dosage forms comprise liquids (solutions, suspensions, and emulsions), semi-solids (pastes), and solids (tablets, capsules, powders, granules, premixes, and medicated blocks).

Some examples of oral dosage forms in the art include, WO90/04391, which discloses an oral dosage form of omega-3 polyunsaturated acids to overcome the problems of vascular diseases. It is known to supply said acids in soft gelatine capsule shells.

EP 2 240 581 B1 discloses a gelatine capsule for pharmaceutical use with a controlled release of active ingredients and a process for the preparation of said gelatine capsules. During said process xylose is added to the liquid gelatine from which afterwards gelatine capsules are formed. Gelatine capsules manufactured according to the process provide retarded release of active ingredients.

U.S. Pat. No. 7,264,824 discloses and oral dosage form for food and food supplements, as well as dietetics comprising polyunsaturated acids in a xylose-hardened gelatine capsule with a retarded release time.

According to some embodiments of the present invention, the compositions described herein may be in a suspension or emulsion.

A suspension is a coarse dispersion of insoluble drug particles, generally with a diameter exceeding 1 µm, in a liquid (usually aqueous) medium. Suspensions are useful for administering insoluble or poorly soluble drugs/components or in situations when the presence of a finely divided form of the material in the GI tract is required. The taste of most drugs is less noticeable in suspension than in solution, due to the drug being less soluble in suspension. Particle size is an important determinant of the dissolution rate and bioavailability of drugs in suspension. In addition to the excipients described above for solutions, suspensions include surfactants and thickening agents. Surfactants wet the solid particles, thereby ensuring the particles disperse readily throughout the liquid. Thickening agents reduce the rate at which particles settle to the bottom of the container. Some settling is acceptable, provided the sediment can be readily dispersed when the container is shaken. Because hard masses of sediment do not satisfy this criterion, caking of suspensions is not acceptable.

An emulsion is a system consisting of 2 immiscible liquid phases, one of which is dispersed throughout the other in the form of fine droplets; droplet diameter generally ranges from 0.1-100 µm. The 2 phases of an emulsion are known as the dispersed phase and the continuous phase. Emulsions are inherently unstable and are stabilized through the use of an emulsifying agent, which prevents coalescence of the dispersed droplets. Creaming, as occurs with milk, also occurs with pharmaceutical emulsions. However, it is not a serious problem because a uniform dispersion returns upon shaking. Creaming is, nonetheless, undesirable because it is associated with an increased likelihood of the droplets coalescing and the emulsion breaking. Other additives include buffers, antioxidants, and preservatives. Emulsions for oral administration are usually oil (the active ingredient) in water, and facilitate the administration of oily substances such as castor oil or liquid paraffin in a more palatable form.

A paste is a 2-component semi-solid in which drug is dispersed as a powder in an aqueous or fatty base. The particle size of the active ingredient in pastes can be as large as 100 µm. The vehicle containing the drug may be water; a polyhydroxy liquid such as glycerin, propylene glycol, or polyethylene glycol; a vegetable oil; or a mineral oil. Other formulation excipients include thickening agents, cosolvents, adsorbents, humectants, and preservatives. The thickening agent may be a naturally occurring material such as acacia or tragacanth, or a synthetic or chemically modified derivative such as xanthum gum or hydroxypropylmethyl cellulose. The degree of cohesiveness, plasticity, and syringeability of pastes is attributed to the thickening agent. It may be necessary to include a cosolvent to increase the solubility of the drug. Syneresis of pastes is a form of instability in which the solid and liquid components of the formulation separate over time; it is prevented by including an adsorbent such as microcrystalline cellulose. A humectant (eg, glycerin or propylene glycol) is used to prevent the paste that collects at the nozzle of the dispenser from forming a hard crust. Microbial growth in the formulation is inhibited using a preservative. It is critical that pastes have a pleasant taste or are tasteless.

A tablet consists of one or more active ingredients and numerous excipients and may be a conventional tablet that is swallowed whole, a chewable tablet, or a modified-release tablet (more commonly referred to as a modified-release bolus due to its large unit size). Conventional and chewable tablets are used to administer drugs to dogs and cats, whereas modified-release boluses are administered to cattle, sheep, and goats. The physical and chemical stability of tablets is generally better than that of liquid dosage forms. The main disadvantages of tablets are the bioavailability of poorly water-soluble drugs or poorly absorbed drugs, and the local irritation of the GI mucosa that some drugs may cause.

A capsule is an oral dosage form usually made from gelatin and filled with an active ingredient and excipients. Two common capsule types are available: hard gelatin capsules for solid-fill formulations, and soft gelatin capsules for liquid-fill or semi-solid-fill formulations. Soft gelatin capsules are suitable for formulating poorly water-soluble drugs because they afford good drug release and absorption by the GI tract. Gelatin capsules are frequently more expensive than tablets but have some advantages. For example, particle size is rarely altered during capsule manufacture, and capsules mask the taste and odor of the active ingredient and protect photolabile ingredients.

A powder is a formulation in which a drug powder is mixed with other powdered excipients to produce a final product for oral administration. Powders have better chemical stability than liquids and dissolve faster than tablets or capsules because disintegration is not an issue. This translates into faster absorption for those drugs characterized by dissolution rate-limited absorption. Unpleasant tastes can be more pronounced with powders than with other dosage forms and can be a particular concern with in-feed powders, in which it contributes to variable ingestion of the dose. Moreover, sick animals often eat less and are therefore not amenable to treatment with in-feed powder formulations. Drug powders are principally used prophylactically in feed, or formulated as a soluble powder for addition to drinking water or milk replacer. Powders have also been formulated with emulsifying agents to facilitate their administration as liquid drenches.

A granule is a dosage form consisting of powder particles that have been aggregated to form a larger mass, usually 2-4 mm in diameter. Granulation overcomes segregation of the different particle sizes during storage and/or dose administration, the latter being a potential source of inaccurate dosing. Granules and powders generally behave similarly; however, granules must deaggregate prior to dissolution and absorption.

A premix is a solid dosage form in which an active ingredient, such as a coccidiostat, production enhancer, or nutritional supplement, is formulated with excipients. Premix products are mixed homogeneously with feed at rates (when expressed on an active ingredient basis) that range from a few milligrams to ~200 g/ton of food/beverage The density, particle size, and geometry of the premix particles should match as closely as possible those of the feed in which the premix will be incorporated to facilitate uniform mixing. Issues such as instability, electrostatic charge, and hygroscopicity must also be addressed. The excipients present in premix formulations include carriers, liquid binders, diluents, anti-caking agents, and anti-dust agents. Carriers, such as wheat middlings, soybean mill run, and rice hulls, bind active ingredients to their surfaces and are important in attaining uniform mixing of the active ingredient. A liquid binding agent, such as a vegetable oil, should be included in the formulation whenever a carrier is used. Diluents increase the bulk of premix formulations, but unlike carriers, do not bind the active ingredients. Examples of diluents include ground limestone, dicalcium phosphate, dextrose, and kaolin. Caking in a premix formulation may be caused by hygroscopic ingredients and is addressed by adding small amounts of anti-caking agents such as calcium silicate, silicon dioxide, and hydrophobic starch. The dust associated with powdered premix formulations can have serious implications for both operator safety and economic losses, and is reduced by including a vegetable oil or light mineral oil in the formulation. An alternate approach to overcoming dust is to granulate the premix formulation.

A medicated block is a compressed feed material that contains an active ingredient, such as a drug, anthelmintic, surfactant (for bloat prevention), or a nutritional supplement, and is commonly packaged in a cardboard box. Ruminants typically have free access to the medicated block over several days, and variable consumption may be problematic. This concern is addressed by ensuring the active ingredient is nontoxic, stable, palatable, and preferably of low solubility. In addition, excipients in the formulation modulate consumption by altering the palatability and/or the hardness of the medicated block. For example, molasses increases palatability and sodium chloride decreases it. Additionally, the incorporation of a binder such as lignin sulfonate in blocks manufactured by compression or magnesium oxide in blocks manufactured by chemical reaction, increases hardness. The hygroscopic nature of molasses in a formulation may also impact the hardness of medicated blocks and is addressed by using appropriate packaging.

In another embodiment, the composition of the present invention is in a chewable oral dosage form. In another embodiment, the chewable oral dosage form is a chewable tablet. In another embodiment, the chewable tablet of the invention is taken slowly by chewing or sucking in the mouth. In another embodiment, the chewable tablet of the invention enables the vitamins contained therein to be orally administered without drinking.

According to some embodiments of the present invention, the composition may comprise any suitable flavor or combination of flavors.

The composition may further comprise other additives, coloring, emulsifiers. The flavors and additives may be of a natural, semi-synthetic, synthetic source or combinations thereof.

In another embodiment of the present invention, the composition further comprises fructose, sorbitol, microcrystalline cellulose, magnesium stearate, or any combination thereof. In another embodiment, the composition further comprises chamomile. In another embodiment, the composition further comprises ginger. In another embodiment, the composition further comprises peppermint. In another embodiment, the composition further comprises anise. In another embodiment, the composition further comprises fennel. In another embodiment, the composition further comprises thyme. In another embodiment, the composition further comprises *Arsenicum album*. In another embodiment, the composition further comprises *Carbo vegetabilis*. In another embodiment, the composition further comprises Ignatia, homeopathic ipecac. In another embodiment, the composition further comprises *Nux vomica*. In another embodiment, the composition further comprises *Zingiber officinale*.

In another embodiment, the composition of the present invention is in the form of a chewing gum product. In another embodiment, chewing gum compositions contemplated by the present invention comprise all types of sugar and sugarless chewing gums and chewing gum formulations known to those skilled in the art, including regular and bubble gum types. In another embodiment, chewing gum compositions of the invention comprise a chewing gum base, a modifier, a bulking agent or sweetener, and one or more other additives such as, flavoring agents, colorants and antioxidants. In another embodiment, the modifying agents are used to soften, plasticize and/or compatibilize one or more of the components of the gum base and/or of the formulation as a whole.

In another embodiment, the present invention provides a soft, chewable dosage form which is pliable and chewy, yet dissolves quickly in the mouth, has a long shelf life, contains little moisture which improves stability and decreases the tendency for the dosage form to dry out, does not require cooking or heating as part of the manufacturing process. In another embodiment, the dosage form is used as a matrix for vitamins.

In another embodiment, the chewable tablet of the invention comprises a metal salt such as calcium, magnesium, aluminum salt, or any mixture thereof. In another embodiment, the chewable tablet of the invention comprises hydroxyalkyl cellulose. In another embodiment, the chewable tablet of the invention comprises low viscosity hydroxyalkyl cellulose. In another embodiment, the chewable tablet of the invention comprises high viscosity hydroxyalkyl cellulose.

In another embodiment, the chewable tablet of the invention comprises various additives. In another embodiment, the chewable tablet of the invention comprises sweeteners. In another embodiment, the chewable tablet of the invention comprises acidic ingredients. In another embodiment, the chewable tablet of the invention comprises taste correctives. In another embodiment, the chewable tablet of the invention comprises polymeric compounds. In another embodiment, the chewable tablet of the invention comprises essential oils.

In another embodiment, the chewable tablet of the invention is a soft tablet. In another embodiment, the chewable tablet of the invention is made in a state of soft candy. In another embodiment, the chewable tablet of the invention is made in a state of jelly.

In another embodiment, the chewable tablet of the invention comprises a core comprising the vitamins of the invention. In another embodiment, the chewable tablet of the invention comprises an outer layer wrapping the core which is made up of chewable base such as a gum, a soft candy or a caramel.

In another embodiment, the compositions of the present invention may be provided in any suitable food of a solid, semi-solid or liquid form.

In another embodiment, the chewable tablet of the invention protects the vitamins that are liable to transform. In another embodiment, the chewable tablet of the invention comprises pectin. In another embodiment, the chewable tablet of the invention comprises maltitol. In another embodiment, the chewable tablet of the invention comprises isomalt. In another embodiment, the chewable tablet of the invention comprises liquid glucose. In another embodiment, the chewable tablet of the invention comprises sugar. In another embodiment, the chewable tablet of the invention comprises citric acid. In another embodiment, the chewable tablet of the invention comprises sorbitol. In another embodiment, the chewable tablet of the invention comprises a flavoring agent. In another embodiment, the chewable tablet of the invention comprises a natural flavoring agent. In another embodiment, the chewable tablet of the invention comprises a synthetic flavor. In another embodiment, the chewable tablet of the invention comprises a volatile oil. In another embodiment, the chewable tablet of the invention comprises synthetic flavor oil. In another embodiment, the chewable tablet of the invention comprises a flavoring aromatic. In another embodiment, the chewable tablet of the invention comprises a oleoresin. In another embodiment, the chewable tablet of the invention comprises an extract derived from a plant. In another embodiment, the chewable tablet of the invention comprises an extract derived from a leaf. In another embodiment, the chewable tablet of the invention comprises an extract derived from a flower. In another embodiment, the chewable tablet of the invention comprises an extract derived from a fruit. In another embodiment, the chewable tablet of the invention comprises an extract derived from a stem.

In another embodiment, the chewable tablet of the invention comprises citrus oil such as but not limited to lime, grapefruit, lemon, or orange. In another embodiment, the chewable tablet of the invention comprises fruit essences such as but not limited to apple, pear, peach, grape, strawberry, raspberry, cherry, plum, pineapple, apricot or other fruit flavors. In another embodiment, the chewable tablet of the invention comprises flavorings such as but not limited to aldehydes and esters such as benzaldehyde (cherry, almond), citral, i.e., alphacitral (lemon, lime), neral, i.e., beta-citral (lemon, lime) decanal (orange, lemon), aldehyde C-8 (citrus fruits), aldehyde C-9 (citrus fruits), adlehyde C-12 (citrus fruits), tolyl aldehyde (cherry, almond), 2,6-dimethyloctanal (green fruit), and 2-dodecenal (citrus, mandarin), mixtures thereof and the like.

In another embodiment, the chewable tablet of the invention comprises a gum. In another embodiment, the chewable tablet of the invention comprises a soft gum. In another embodiment, the chewable tablet of the invention comprises nougat. In another embodiment, the chewable tablet of the invention comprises soft candy. In another embodiment, the chewable tablet of the invention comprises hard candy. In another embodiment, the chewable tablet of the invention comprises caramel. In another embodiment, the chewable tablet of the invention comprises an enhancing agent of chewing property.

In another embodiment, sugar used in the present invention may be selected from the group consisting of white sugar, liquid glucose, sorbitol, dextrose, isomalt, liquid maltitol, aspartame and lactose, and this sugar may comprise 30-90 weight % by total weight of the ingredients.

In another embodiment, the chewable tablet of the invention comprises a sweetener such as but not limited to: glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as suralose; sugar alcohols such as sorbitol, mannitol, xylitol, and the like. In another embodiment, the chewable tablet of the invention comprises hydrogenated starch hydrolysates and the synthetic sweetener 3,6-dihydro-6-methyl-1-1-1,2,3-oxathiazin-4-one-2,2-dioxide. In another embodiment, the chewable tablet of the invention comprises the potassium salt (acesulfame-K), and sodium and calcium salts of 3,6-dihydro-6-methyl-1-1-1,2,3-oxathiazin-4-one-2, 2-dioxide. In another embodiment, the chewable tablet of the invention comprises other sweeteners known to one of skill in the art.

In another embodiment, glycerin, lecithin, hydrogenated palm oil or glyceryl monostearate are used as a protecting agent of crystallization of the sugars in 0.02-3.0 weight % by total weight of the ingredients, to prevent adhesion to oral cavity and improve the soft property of the products.

In another embodiment, isomalt or liquid maltitol are used as an enhancing agent of chewing property. In another embodiment, gelatin or arabic gum are used as a keeping agent of hardness and extension property in 0.1-3.0 weight % by total weight of the ingredients. In another embodiment, food flavor or a fruits extract; a souring agent such as citric acid are added in adequate amount. In another embodiment, a coloring agent such as a food color is optionally added in a small amount.

Yet a further embodiment of the present invention includes the use of an effervescent disintegration agent. In another embodiment, its action aids in the masking of objectionable taste of the vitamins.

In another embodiment, of the present invention the effervescent disintegration agent is an acid. In another embodiment, of the present invention the effervescent disintegration agent is citric acid. In another embodiment, of the present invention the effervescent disintegration agent is tartaric acid. In another embodiment, of the present invention the effervescent disintegration agent is malic acid. In another embodiment, of the present invention the effervescent disintegration agent is fumaric acid. In another embodiment, of the present invention the effervescent disintegration agent is adipic acid. In another embodiment, of the present invention the effervescent disintegration agent is succinic acid. In another embodiment, of the present invention the effervescent disintegration agent is at least one base such as but not limited to: carbonate salts, bicarbonate salts and mixtures thereof.

In another embodiment, the chewable tablet of the invention comprises a crystallization modifier such but not limited to, surfactants (Spans™ and Tweens™), dextrose, polyethylene glycol (PEG), polypropylene glycol (PPG), etc. These modifiers generally provide controlled acceleration of crystallization while the matrix is bound. In another embodiment, these crystallization modifiers enhance the formation of a crystalline frame and the conversion of the remaining mass.

In another embodiment, crystallization modifiers are surfactants having a hydrophilic to lipid balance (HLB) of six or greater, i.e., they have the same degree of hydrophilicity as surfactants characterized by degree of HLB. In another embodiment, such materials include, but are not limited to anionic, cationic and zwitterionic surfactants as well as neutral materials which have an HLB of six or greater. In another embodiment, crystallization modifiers are hydrophilic materials having polyethylene oxide linkages. In another embodiment, crystallization modifiers have a molecular weight of at least 100.

In another embodiment, the chewable tablet of the invention comprises a filler. In another embodiment, filler increases the bulk of the tablet. In another embodiment, the filler is calcium sulfate, both di- and tri basic, starch, calcium carbonate, microcrystalline cellulose, modified starches, lactose, sucrose, mannitol, sorbitol, or any combination thereof.

In another embodiment, the chewable tablet of the invention comprises a binder such as but not limited to: starches, pre-gelatinize starches, gelatin, polyvinylpyrrolidone, methylcellulose, sodium carboxymethylcellulose, ethylcellulose, polyacrylamides, polyvinyloxoazolidone, and polyvinylalcohols.

In another embodiment, the chewable tablet of the invention comprises a lubricant such as but not limited to: magnesium stearate, calcium stearate, zinc stearate, hydrogenated vegetable oils, sterotex, polyoxyethylene, monostearate, talc, polyethyleneglycol, sodium benzoate, sodium lauryl sulfate, magnesium lauryl sulfate and light mineral oil.

In another embodiment, the chewable tablet of the invention comprises a dispersion enhancer such as but not limited to: starch, alginic acid, polyvinylpyrrolidones, guar gum, partially hydrolyzed guar gum, kaolin, bentonite, purified wood cellulose, sodium starch glycolate, isoamorphous silicate, and microcrystalline cellulose as high HLB emulsifier surfactants.

In another embodiment, the chewable tablet of the invention comprises a disintegrant such as but not limited to: Croscarmellose sodium, marketed under the trade name Ac-Di-Sol.

In another embodiment, the chewable tablet of the invention comprises an absorbent such as but not limited to: maltodextrin. In another embodiment, the chewable tablet of the invention comprises an emulsifier such as but not limited to: Mono- and diglycerides, Oleaginous substances such as food oils like Medium, Chain Triglycerides (MCT), and Stearine D 17.

In another embodiment, the chewable tablet of the invention comprises a water soluble bulking agent such as but not limited to: hydrocolloid thickeners and binders, such as gum arabic, pectins, modified starches, alginates, carrageenans, xanthan gums, carboxymethylcellulose, methylcellulose, hydroxyethylcellulose, hydroxypropylcellulose, hydroxypropylmethylcellulose, propylene glycol alginate, polyvinylpyrrolidone (PVP), carboxyvinyl polymers (such as Carbopol®), polyethylene oxide polymers (such as Polyox®), sorbitol, xylitol, sucrose, fructose, dextrose, mannitol, starch maltodextrin, corn syrup solids, or combinations thereof.

In another embodiment, the chewable tablet of the invention comprises a water insoluble bulking agent such as but not limited to: talc, dicalcium phosphate, powdered celluloses, microcrystalline celluloses and antacid compounds.

In another embodiment, the chewable tablet of the invention comprises vitamins in compressed particles. In another embodiment, individual particles are coated with a blend of cellulose acetate or cellulose acetate butyrate and polyvinyl pyrrolidone (USP Povidone or "PVP"). In another embodiment, the coating provides excellent taste masking while still permitting acceptable bioavailability of the vitamins. In another embodiment, the chewable tablet In another embodiment, the invention relates to a composition of the invention comprised within chewable and edible soft gelatin capsules, the shells of which comprise gelatin, water, plasticizer and a hydrogenated starch hydrolysate. In another embodiment, soft gelatin shell comprises about 10-45% gelatin; about 5-30% water; about 12-35% plasticizer; and about 2-25% of a hydrogenated starch hydrolysate. In another embodiment, the shell encloses a soft gelatin capsule fill material. In another embodiment, the gelatin may be of Type A, Type B, or a mixture thereof. In another embodiment, in order to augment the taste and chewability of the capsule shell, as well as to assist in the rapid dissolution of the shell upon chewing, the present capsule shell further comprises a hydrogenated starch hydrolysate.

In another embodiment, chewable systems of the invention are preferable for administering the vitamins of the invention. In another embodiment, the act of chewing increases the surface area of the vitamins and increases the rate of absorption by the digestive tract. In another embodiment, chewable systems of the invention provide vitamin, topically to the mouth or throat areas for both local effects and systemic absorption.

The preparation of pharmaceutical compositions that contain vitamins, for example by mixing, granulating, or tablet-forming processes, is well understood in the art. The vitamins are often mixed with excipients that are pharmaceutically acceptable and compatible with the active ingredient. For oral administration, the active ingredients of compositions of the present invention are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

In another embodiment, additional methods of administering the vitamins of the invention comprise injectable dosage forms. In another embodiment, the injectable is administered intraperitonealy. In another embodiment, the injectable is administered intramuscularly. In another embodiment, the injectable is administered intradermally. In another embodiment, the injectable is administered intravenously. Each possibility represents a separate embodiment of the present invention.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intramuscularly and are thus formulated in a form suitable for intra-muscular administration.

In another embodiment, additional methods of administering the vitamins of the invention comprise dispersions, suspensions or emulsions. In another embodiment, the dispersion, suspension or emulsion is administered orally. In another embodiment, the solution is administered by infusion. In another embodiment, the solution is a solution for inhalation. Each possibility represents a separate embodiment of the present invention.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active compound agent over a period of time. Each possibility represents a separate embodiment of the present invention.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs. Each possibility represents a separate embodiment of the present invention.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs. Each possibility represents a separate embodiment of the present invention.

In another embodiment, the pharmaceutical compositions provided herein are controlled-release compositions, i.e. compositions in which the active compounds are released over a period of time after administration. Controlled- or sustained-release compositions include formulation in lipophilic depots (e.g. fatty acids, waxes, oils). In another embodiment, the composition is an immediate-release composition, i.e. a composition in which all the active compound is released immediately after administration. Each possibility represents a separate embodiment of the present invention.

In another embodiment, the pharmaceutical composition is delivered in a controlled release system. In another embodiment, the agents are administered using intravenous infusion, an implantable osmotic pump, a transdermal patch, liposomes, or other modes of administration. In another embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the therapeutic target, thus requiring only a fraction of the systemic dose (see, e.g., Goodson, in Medical Applications of Controlled Release, supra, vol. 2, pp. 115-138 (1984); and Langer R, Science 249: 1527-1533 (1990). Each possibility represents a separate embodiment of the present invention.

The compositions also include, in another embodiment, incorporation of the active materials into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance. Each possibility represents a separate embodiment of the present invention.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors. Each possibility represents a separate embodiment of the present invention.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications also increase, in another embodiment, the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound. Each possibility represents a separate embodiment of the present invention.

The compositions of the present invention may comprise one or more additional components may further include an additional component selected from the group consisting of an anti-static agent, a buffering agent, a bulking agent, a chelating agent, a colorant, a diluent, a dye, an emollient, a fragrance, an occlusive agent, a pH-adjusting agent, a preservative, and a vitamin.

The compositions of the present invention may comprise one or more additional active agents, selected from the group consisting of active herbal extracts, analgesics, anti-allergic agents, anti-aging agents, anti-bacterials, antibiotic agents, anticancer agents, antidandruff agents, antidepressants, antidermatitis agents, anti-edemics, antihistamines, anti-helminths, anti-hyperkeratolyte agents, anti-inflammatory agents, anti-irritants, anti-microbials, anti-mycotics, anti-proliferative agents, antioxidants, anti-wrinkle agents, anti-pruritics, antiseptic agents, antiviral agents, anti-yeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, keratolytic agents, lactams, metals, metal oxides, mitocides, neuropeptides, non-steroidal anti-inflammatory agents, oxidizing agents, photodynamic therapy agents, retinoids, sanatives, scabicides, self tanning agents, skin whitening agents, vasoconstrictors, vasodilators, vitamins, vitamin D derivatives and wound healing agents.

According to some embodiments, the composition may comprise one or more anti-oxidants/radical scavengers. The anti-oxidant/radical scavenger may be selected from butylated hydroxy benzoic acids and their salts, coenzyme Q10, coenzyme A, gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

According to some embodiments, the composition may comprise one or more additional vitamins selected from vitamin A, any one or more of the vitamin B complex, vitamin D and vitamin K.

According to some additional embodiments, the composition may comprise one or more of rutin, bromelain, trypsin, an essential amino acid, a horse chestnut extract, a butcher's broom extract, a gotu kola extract, a ginko extract, a ginseng extract, a hawthorn extract, a rose hip extract and a bioflavenoid.

The preparation of pharmaceutical compositions that contain the vitamins of the invention are performed, for example by mixing, granulating, or tablet-forming processes, is well understood in the art. The active therapeutic ingredient is often mixed with excipients that are pharmaceutically acceptable and compatible with the active ingredient. For oral administration, the active compounds are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the active compounds are converted into a solution, suspension, or emulsion, if desired with the substances customary and suitable for this purpose, for example, solubilizers or other substances.

According to some additional embodiments, the composition may comprise one or more of bran oil, gelatin, glycerin, water, red palm fruit oil and carob extract.

According to some further embodiments, the composition may be formulated in the form of a drink or beverage.

According to some further embodiments, the composition may be formulated in the form of a sweet, candy, lozenge, chewing gum, toffee, candy bar, chocolate bar, health snack or other appetizing food product.

Each of the above additives, excipients, formulations and methods of administration represents a separate embodiment of the present invention.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to inducing remission. In another embodiment, "treating" refers to slowing the progression of a disease.

Some embodiments of the present invention are directed to for treating and/or preventing heart disease, such as, but not limited to, atherosclerotic and hypertensive diseases, congenital heart disease, rheumatic heart disease; the method comprising administering to a human subject a composition comprising:
a. Vitamin C;
b. Vitamin E;
c. Omega-3 fatty acids; and
d. Omega-6 fatty acids;
so as to treat or prevent said heart disease.

In further embodiments of the present invention, methods are provided for treating and/or preventing peripheral blood vessel disorders, the method comprising: administering to a human subject a composition comprising:
a. Vitamin C;
b. Vitamin E;
c. Omega-3 fatty acids; and
d. Omega-6 fatty acids;
so as to treat or prevent said peripheral blood vessel disorder.

In additional embodiments of the present invention, a composition is provided for treating and/or preventing various diseases or disorders, the composition comprising:
a. Vitamin C;
b. Vitamin E; and
c. at least one Omega-3 fatty acid.

In additional embodiments of the present invention, a composition is provided for treating and/or preventing various diseases or disorders, the composition comprising:
a. Vitamin C;
b. Vitamin E; and
c. at least one Omega-6 fatty acid.

In additional embodiments of the present invention, a composition is provided for treating and/or preventing various diseases or disorders, the composition comprising:
a. Vitamin C;
b. Vitamin E;
c. at least one Omega-3 fatty acid; and
d. at least one Omega-6 fatty acid.

In additional embodiments of the present invention, a composition is provided for treating and/or preventing various diseases or disorders, the composition comprising:
a. 10-3000 mg vitamin C;
b. 10-1000 IU Vitamin E;
c. 1-1000 mg Omega-3 fatty acids; and
d. 1-100 mg Omega-6 fatty acids.

In additional embodiments of the present invention, an oral dosage form is provided for treating and/or preventing various diseases or disorders, the oral dosage form comprising:
a. 10-3000 mg vitamin C;
b. 10-1000 IU Vitamin E;
c. 1-1000 mg Omega-3 fatty acids; and
d. 1-100 mg Omega-6 fatty acids.

In additional embodiments of the present invention, an oral dosage form is provided for treating and/or preventing various diseases or disorders, the oral dosage form comprising:
a. 20-1000 mg vitamin C;
b. 20-500 IU Vitamin E;
c. 20-500 mg Omega-3 fatty acids; and
d. 5-50 mg Omega-6 fatty acids.

In additional embodiments of the present invention, a method is provided for treating and/or preventing a disorder or a disease comprising: administering an oral dosage form to a human subject, the oral dosage form comprising:
a. 20-1000 mg vitamin C;
b. 20-500 IU Vitamin E;
c. 20-500 mg Omega-3 fatty acids; and
d. 5-50 mg Omega-6 fatty acids,
so as to treat or prevent the disorder or disease.

According to some embodiments the method further comprises repeatedly administering the oral dosage form to the human.

Experimental Details Section

Example 1

A Capsule for Treating Varicose Veins

Materials and Experimental Methods
An effective capsule tablet for treating blood circulatory disorders such as varicose veins was prepared. The active ingredients included:
vitamin C: 500 mg
vitamin E: 500 IU
Omega-3 fatty acids 200 mg
Omega-6 fatty acids 20 mg.

Example 2

A Process of Making a Capsule for Treating Varicose Veins

Materials and Experimental Methods
Capsules comprising the vitamins of the invention for treating blood circulation disorders, such as varicose veins, were prepared as follows:
Phase A: A standard 1 g two-sectioned drug capsule. One example of the capsule is a OceanCaps™ fish gelatin capsule, available Great Abington, Cambridge, United Kingdom. Another example of a drug capsule is a Coni-Snap® capsule, also available from Capsugel.
Phase B: vitamin C (200 mg), vitamin E (200 IU). Omega-3 fatty acids (20 mg) and Omega-6 fatty acids (5 mg). A homogenous powder blend of Phase B was obtained by mixing the ingredients for 40 minutes to form a mixture.
In this example, the omega-6 fatty acids were obtained from a nut source. The omega-3 fatty acids were obtained from a fish source.
The mixture of phase B was encapsulated by the capsule of phase A by standard techniques known in the art.

Example 3

A Process of Making a Chewable Tablet for Treating Varicose Veins

Materials and Experimental Methods
Chewable tablets comprising the vitamins of the invention for treating blood circulation disorders, such as varicose veins, were prepared as follows:
Phase A: 1250 mg fructose powder, 862 mg sorbitol granules, 37.5 mg microcrystalline cellulose, 50 mg magnesium stearate, 50 mg lemon fresh flavor, 37.5 mg citric acid, 12.5 mg natural chlorophyll color. A homogenous powder blend of Phase A was obtained by mixing the ingredients of phase A.
Phase B: vitamin C (500 mg), vitamin E (200 IU, around 400 mg). Omega-3 fatty acids (200 mg) and Omega-6 fatty acids (20 mg). A homogenous powder blend of Phase B was obtained by mixing the ingredients for 40 minutes to form a mixture. The mixtures of phase B were mixed with the homogenous powder blend of Phase A for 40 minutes.
Phase C: Chewable tablets were prepared in a tableting machine. Each tablet weighed about 3.4 g (±10%).

Example 4

Treatment of Varicose Veins in Women Taking One Capsule/Day (Example 2)

A number of women, who suffer from varicose veins, were provided with capsules, as prepared in Example 2 hereinabove, and were advised to take one capsule per day over extended periods of time and to report on any changes in their feelings and wellbeing. Table 1 provides results of a sample of responses from women in the group.

TABLE 1

Effects of taking capsules over time in women volunteers

| Volunteer number | Number of tablets/day | Duration of use | Age of volunteer | Reported effects on varicose veins |
|---|---|---|---|---|
| 1 | 1 | 3 weeks | 26 | Much improved feeling in legs, less pain, improved visual appearance of varicose veins. |
| 2 | 1 | Two months | 28 | Significant pains due to varicose veins disappeared after taking capsules for around a month in third trimester of pregnancy. Improved feeling in veins, though varicose veins did not disappear, but did improve in visual appearance. |
| 2 | 1 | Four additional months | | Pains disappeared, slight improvement in the appearance of the veins |
| 3 | 1 | One-two months | 34 | Reduction in pain due to varicose veins, improved visual appearance of varicose veins |
| 4 | 1 | Two months | 39 | Reduction in swelling, pain, itching after a month of taking capsules during third trimester of pregnancy. Significant improvement after birth and veins did not demonstrate the previous venous insufficiency, though varicose veins did not disappear, but did improve in visual appearance. |

It can thus be seen that the medicaments of the present invention are useful in treating varicose veins.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

What is claimed is:

1. A method for ameliorating symptoms of a leg vein disease or disorder in a mammalian subject, the method comprising administering a composition wherein the active ingredients of said composition consist of:
   i. vitamin C,
   ii. vitamin E, and
   iii. at least one omega-3 fatty acid and at least one omega-6 fatty acid,
   to said mammalian subject in a pharmaceutically effective amount so as to treat the disease or disorder, wherein said disease or disorder comprises at least one of varicose veins and swelling of the legs.

2. The method according to claim 1, wherein the:
   a. vitamin C is in an amount of 10-3000 mg,
   b. vitamin E is in an amount of 10-1000 IU,
   c. the omega-3 fatty acid is in an amount of 1-1000 mg, and
   d. the omega-6 fatty acid is in an amount of 1-100 mg.

3. The method according to claim 2, wherein the:
   a. vitamin C is in an amount of 20-1000 mg,
   b. vitamin E is in an amount of 20-500 IU,
   c. omega-3 fatty acid is in an amount of 20-500 mg, and
   d. omega-6 fatty acid is in an amount of 5-50 mg.

4. The method according to claim 3, wherein the:
   a. vitamin C is in an amount of 200-500 mg,
   b. vitamin E is in an amount of 200-500 IU,
   c. omega-3 fatty acid is in an amount of 20-200, and
   d. omega-6 fatty acid is in an amount of 5-20 mg.

5. The method according to claim 1, wherein the omega 3 fatty acid is selected from eicosapentaenoic acid (EPA (20:5)), Eicosatetraenoic acid (ETA), and docosahexaenoic acid (DHA (22:6)).

6. The method according to claim 1, wherein the omega 6 fatty acid is selected from gamma-linolenic acid (GLA (18:3)), dihomo-gamma-linolenic acid, (DGLA (20:3)) and arachidonic acid (AA (20:4)).

7. The method according to claim 1, wherein said composition is in an oral dosage form.

8. The method according to claim 7, wherein said oral dosage form is selected from a capsule and a chewable tablet.

9. A method for reducing the incidence of a leg vein disease or disorder in a subject who suffers from said leg vein disease or disorder the method comprising administering a composition wherein the active ingredients of said composition consist of:
   i. vitamin C,
   ii. vitamin E, and
   iii. at least one omega-3 fatty acid and at least one omega-6 fatty acid,
   to said mammalian subject in a pharmaceutically effective amount so as to reduce the incidence of said disease or disorder in said subject.

10. The method according to claim 9, wherein the:
    a. vitamin C is in an amount of 10-3000 mg,
    b. vitamin E is in an amount of 10-1000 IU,
    c. omega-3 fatty acid is in an amount of 1-1000 mg, and
    d. omega-6 fatty acid is in an amount of 1-100 mg.

11. The method according to claim 10, wherein the:
    a. vitamin C is in an amount of 20-1000 mg,
    b. vitamin E is in an amount of 20-500 IU,
    c. omega-3 fatty acid is in an amount of 20-500 mg, and
    d. omega-6 fatty acid is in an amount of 5-50 mg.

12. The method according to claim 11, wherein the:
    a. vitamin C is in an amount of 200-500 mg,
    b. vitamin E is in an amount of 200-500 IU,
    c. omega-3 fatty acid is in an amount of 20-200 mg, and
    d. omega-6 fatty acid is in an amount of 5-20 mg.

13. The method according to claim 9, wherein the omega 3 fatty acid is selected from eicosapentaenoic acid (EPA (20:5)), Eicosatetraenoic acid (ETA), and docosahexaenoic acid (DHA (22:6)).

14. The method according to claim 9, wherein the omega 6 fatty acid is selected from gamma-linolenic acid (GLA (18:3)), dihomo-gamma-linolenic acid, (DGLA (20:3)) and arachidonic acid (AA (20:4)).

15. The method according to claim 9, wherein the disease or disorder comprises at least one of varicose veins, spider veins, and swelling of the legs.

16. The method according to claim 9, wherein said composition is in an oral dosage form.

17. The method according to claim 16, wherein said oral dosage form is selected from a capsule and a chewable tablet.

18. A method for ameliorating symptoms of spider veins in a mammalian subject, the method comprising administering a composition wherein the active ingredients of said composition consist of:
   i. 200-500 mg of Vitamin C,
   ii. 200-500 IU of Vitamin E,
   iii. 20-200 mg of Omega-3 fatty acid, and
   iv. 5-20 mg of Omega-6 fatty acid,
   to said mammalian subject in a pharmaceutically effective amount so as to ameliorate symptoms of spider veins.

19. The method according to claim 18, wherein the omega-3 fatty acid is selected from eicosapentaenoic acid (EPA (20:5)), Eicosatetraenoic acid (ETA), and docosahexaenoic acid (DHA (22:6)).

20. The method according to claim 18, wherein the omega-6 fatty acid is selected from gamma-linolenic acid (GLA (18:3)), dihomo-gamma-linolenic acid, (DGLA (20:3)) and arachidonic acid (AA (20:4)).

21. The method according to claim 18, wherein said composition is in an oral dosage form.

22. The method according to claim 21, wherein said oral dosage form is selected from a capsule and a chewable tablet.

23. The method according to claim 1, wherein said composition includes non-active ingredient additives.

24. The method according to claim 23, wherein said non-active ingredient additive are selected from the group consisting of vehicles, stabilizers, dispersion enhancers, disintegrants, emulsifiers, absorbants and inert diluents.

25. The method according to claim 24, wherein said dispersion enhancer is selected from the group consisting of starch, alginic acid, polyvinylpyrrolidones, guar gum, partially hydrolyzed guar gum, kaolin, bentonite, purified wood cellulose, sodium starch glycolate, isoamorphous silicate, and microcrystalline cellulose.

26. The method according to claim 24, wherein said disintegrant comprises croscamellose sodium.

27. The method according to claim 24, wherein said absorbent comprises maltodextrin.

28. The method according to claim 24, wherein said an emulsifier is selected from the group comprising mono- and diglycerides, food oils and medium chain triglycerides (MCT).

29. The method according to claim 9, wherein said composition includes non-active ingredient additives.

30. The method according to claim 29, wherein said non-active ingredient additive are selected from the group consisting of vehicles, stabilizers, dispersion enhancers, disintegrants, emulsifiers, absorbants and inert diluents.

31. The method according to claim 30, wherein said dispersion enhancer is selected from the group consisting of starch, alginic acid, polyvinylpyrrolidones, guar gum, partially hydrolyzed guar gum, kaolin, bentonite, purified wood cellulose, sodium starch glycolate, isoamorphous silicate, and microcrystalline cellulose.

32. The method according to claim 30, wherein said disintegrant comprises croscamellose sodium.

33. The method according to claim 30, wherein said absorbent comprises maltodextrin.

34. The method according to claim 30, wherein said an emulsifier is selected from the group comprising mono- and diglycerides, food oils and medium chain triglycerides (MCT).

35. The method according to claim 18, wherein said composition includes non-active ingredient additives.

36. The method according to claim 35, wherein said non-active ingredient additive are selected from the group consisting of vehicles, stabilizers, dispersion enhancers, disintegrants, emulsifiers, absorbants and inert diluents.

37. The method according to claim 36, wherein said dispersion enhancer is selected from the group consisting of starch, alginic acid, polyvinylpyrrolidones, guar gum, partially hydrolyzed guar gum, kaolin, bentonite, purified wood cellulose, sodium starch glycolate, isoamorphous silicate, and microcrystalline cellulose.

38. The method according to claim 36, wherein said disintegrant comprises croscamellose sodium.

39. The method according to claim 36, wherein said absorbent comprises maltodextrin.

40. The method according to claim 36, wherein said an emulsifier is selected from the group comprising mono- and diglycerides, food oils and medium chain triglycerides (MCT).

* * * * *